(12) United States Patent
Magnuson-Hawkins

(10) Patent No.: US 6,290,992 B1
(45) Date of Patent: Sep. 18, 2001

(54) FOAM FORMULATION FOR TERMITE CONTROL AND METHOD OF APPLICATION THEREFOR

(76) Inventor: Shelby J. Magnuson-Hawkins, 5664 Paseo de la Tirada, Tucson, AZ (US) 85750

( * ) Notice: Subject to any disclaimer, the term of this patent is extended or adjusted under 35 U.S.C. 154(b) by 0 days.

(21) Appl. No.: 09/113,763

(22) Filed: Jul. 10, 1998

Related U.S. Application Data

(63) Continuation-in-part of application No. 08/800,298, filed on Feb. 13, 1997, now abandoned.
(60) Provisional application No. 60/011,554, filed on Feb. 13, 1996.

(51) Int. Cl.$^7$ .......................... A01N 25/16; A01N 47/10; A01N 47/18; A01N 53/00; A01N 55/08
(52) U.S. Cl. .................. 424/660; 424/43; 424/405; 424/407; 424/657; 424/658; 424/659; 424/DIG. 11; 514/64; 514/65; 514/68; 514/477; 514/478; 514/479; 514/480; 514/481; 514/483; 514/519; 514/521; 514/531; 514/945
(58) Field of Search ................. 424/405, DIG. 11, 424/43, 407, 657–660; 514/945, 64, 65, 68, 477–481, 483, 519, 521, 531

(56) References Cited

U.S. PATENT DOCUMENTS

| | | | |
|---|---|---|---|
| 3,858,346 | 1/1975 | Bailey | 43/124 |
| 4,344,963 | 8/1982 | Fuchs et al. | 514/521 |
| 5,089,483 | 2/1992 | Tsuda et al. | 514/64 |
| 5,196,407 | 3/1993 | Goletz et al. | 514/63 |
| 5,207,823 | 5/1993 | Shiozawa | 106/18.13 |
| 5,270,108 | 12/1993 | Savoy | 428/305.5 |
| 5,346,699 | 9/1994 | Tiernan et al. | 424/405 |
| 5,373,674 | 12/1994 | Winter, IV | 52/309.9 |
| 5,804,641 * | 9/1998 | Iwakawa | 524/507 |
| 5,881,493 * | 3/1999 | Restive | 43/124 |
| B1 5,346,699 * | 7/1998 | Tiernan et al. | 424/405 |

FOREIGN PATENT DOCUMENTS

| | | |
|---|---|---|
| 11789 | 6/1980 | (EP) . |
| 2038636 | 7/1980 | (GB) . |

OTHER PUBLICATIONS

Dlugoss, Mark, "Controlling termites with foam," Pest Control, p. 42, Nov. 1994.*

Ware, George W., "Complete Guide to Pest Control—With and Without Chemicals," Thomson Publications, CA, 1980, p. 153.

* cited by examiner

Primary Examiner—John Pak
(74) Attorney, Agent, or Firm—Antonio R. Durando

(57) ABSTRACT

A method of termite control consists of injecting a foam formulation above ground into the walls of a structure infested with termites or other undesirable pests. The inner spaces of affected walls are flooded at and above ground level to ensure that the foam formulation reaches all passages open to the soil under the structure and establishes an above-ground layer of pest-control chemicals. The foam penetrates all porous material exposed to the injection and impregnates it with active ingredients that remain embedded in the material long after the foam disappears, thereby retaining the insecticidal, repellant and preservative properties of the active agents for a long time without exposure to normal degrading forces. The pest-control formulation preferably comprises pesticide, repellant and preservative components, and a foaming agent in a liquid carrier. The components are mixed with air to produce a foam that is injected directly into the inner spaces of walls, floors, ceilings or other above-ground structural members of the infested building. The foam is formulated with the objective of maximizing its absorption into the treated wood.

13 Claims, 1 Drawing Sheet

FOAM FORMULATION FOR TERMITE CONTROL AND METHOD OF APPLICATION THEREFOR

CROSS-REFERENCE TO RELATED APPLICATIONS

This application is a continuation-in-part application of U.S. Ser. No. 08/800,298, filed Feb. 13, 1997, now abandoned, which is based on Provisional Application Ser. No. 60/011,554, filed Feb. 13, 1996.

BACKGROUND OF THE INVENTION

1. Field of the Invention

The present invention relates to a method for controlling destructive pest infestations. More particularly, the invention relates to a new chemical formulation and a novel method of application to wood structures for combatting termites and other pests and for providing a continuing repellant effect against further infestations.

2. Description of the Prior Art

The conventional methods for combatting insect infestations are sub-slab and perimeter soil injection, subsoil bait stations, and fumigation. Sub-slab and perimeter treatments involve injection of an insecticidal composition into the soil below or around the foundation of structures. Though effective when strong insecticides are used, these methods pose environmental hazards because of the toxicity of the chemicals injected into the ground, especially when the ground below the structure is porous, and/or when an aquifer is relatively close to the surface. Therefore, laws and regulations have severely limited the ability to use the most effective pest-control agents, such as Chevron's Chloradane®. Moreover, dispersal of the insecticidal active ingredients in the environment through runoff and natural breakdown gradually reduces the effectiveness of the treatment in preventing further infestations.

Soil treatment methods involve the application of a chemical termiticide to the ground around the foundation of a structure. The goal of this application is to create a barrier that kills any termites coming into contact with it, thus preventing their entry into the structure. One major problem with using this method is the fact that the chemicals used tend to rapidly break down so that the barrier is ineffective within a relatively short period of time (2 years or less), prompting the need for expensive retreatment. Secondly, barrier treatments using soil termiticides generally do not affect populations of subterranean termite colonies (prevalent in hot, arid regions), which may be able to tunnel through or otherwise avoid the treated area.

The colony baiting methods of termite control typically involve adding a slow acting toxicant to a source of food with the idea of inhibiting the growth of or otherwise poisoning the entire colony. Limitations of the baiting methods revolve around the need for termites to first find, and then continue feeding on, the treated wood. If termites begin to avoid treated bait or if the entire colony is not eradicated, the termite population may in fact increase in or around the treatment area due to unchecked growth or to the foundation of supplemental colonies.

Fumigation involves the delivery of termiticides or other chemicals in aerosol form in an enclosure enveloping the building being treated. As such, it poses environmental problems resulting from chemical exposure to humans, animals and vegetation. Furthermore, fumigation leaves no residual and accordingly does not provide long-lasting protection.

Various pest-control and preservative compositions have been described in prior patents. For example, U.S. Pat. No. 5,196,407 to Goletz et al. (1993) discloses a composition comprising a fungicidal carbamate used for preserving wood and wood material. An insecticide may also be included in this composition. U.S. Pat. No. 5,207,823 to Shiozawa (1994) describes a wood preservative composition comprising copper borate and zinc borate as the active principles in a volatile basic carrier. In U.S. Pat. No. 5,089,483 (1992), Tsuda et al. disclose the use of alkyldimethylamine tetraborate as an effective antidecay and antitermite agent for timber.

A known class of useful pesticidal compounds consists of pyrethroids, synthetic substances related to pyrethrins. Characterized by a 2-phenyl-alk-1-enyl-cyclopropane-carboxylic acid ester core, pyrethroids include the effective insecticides bifenthrin and permethrin. U.S. Pat. No. 4,344,963, issued to Fuchs et al. (1982); European Patent Application No. 11,789, published Nov. 19, 1979; and UK Patent Application No. GB 2,038,636, published Jul. 30, 1980, all describe pyrethroids as useful insecticides and acaricides.

Building materials pretreated with borates are also known. U.S. Pat. No. 5,270,108, issued to Savoy (1993), discloses a building material with a foam core bonded to exterior skins of oriented strand board. The core is treated with a sodium borate compound to preserve the building material from insect, mold, and fungi attack. U.S. Pat. No. 5,373,674 to Winter (1994) describes another prefabricated building panel that includes an insulative core. Borate may be incorporated or encapsulated within the core.

In U.S. Pat. No. 3,858,346 (1975), Bailey teaches the combination of termite-attracting baits with the impregnation of exposed lower structure timbers with a liquid carrying a termiticide. Finally, in U.S. Pat. No. 5,346,699 (1994), Tiernan et al. disclose the concept of injecting a pesticide in foam form under the slab of a structure for the purpose of saturating the ground and all open passages to the structure from underneath the slab. The technique is directed to reaching and depositing active ingredients on the surface of all affected structural materials.

None of these inventions, taken alone or in combination, address the issues of treating the material in a building with the idea of not only exterminating the termites present at the sites but also repelling them from their food source to prevent future infestations. In addition, because of the necessity of contaminating the soil, no prior-art method is environmentally innocuous. Therefore, a need still exists for an environmentally sensitive, yet effective and long-lasting method for combating pest infestations in a manner that provides long-term protection against renewed attacks.

SUMMARY OF THE INVENTION

Accordingly, it is a principal object of the invention to provide a method for treating structures containing wood (or wallboard, hollow bricks or other porous stock subject to attack by termites, hereinafter collectively referred to as wood), such that the wood becomes undesirable as a food source for the termites.

Another goal of the invention is to treat the wood and other edible components within the structure so that they continue to repel infesting pests, especially termites, thereby providing long-lasting protection from future infestations.

Another objective is a pest-control composition that also provides a preservative effect on the wood of the structures being treated.

An additional object of the invention is a method of application that makes it possible to deliver the active ingredients of the pest-control composition to all wood surfaces subject to attack by termites, or other pest being controlled, and to all open passages that provide access to the interior of the structure from underground and exterior sources.

Still another object is to achieve the above objectives using a fluid foam carrier that flows to reach and impregnate all wood structures in need of protection and that, upon defoaming, leaves a continuous protective layer of impregnated material.

A further goal is a method of delivery that can be carried out by injection in a manner compatible with the other objectives of the invention.

Another object of the invention is a method for combatting interior-structure infestations that is relatively safe and environmentally friendly by avoiding sub-slab or perimeter injection of chemicals into the ground and airborne fumigation of chemicals.

Finally, a goal is the implementation of the above mentioned objectives in a commercially viable system that maximizes the utilization of existing technology and results in an economic, safe, and commercially viable pest-control system.

In accordance with these and other objectives, this invention consists of injecting a pest-control foam formulation above ground into the walls of a structure infested with termites or other undesirable pests. The inner spaces of affected walls are flooded at and above ground level to ensure that the foam formulation reaches all passages to the soil under the structure and establishes an above-ground layer of pest-control chemicals. The foam penetrates all porous materials exposed to the injection and impregnates them with active ingredients that remain embedded in the materials long after the foam disappears, thereby retaining the insecticidal, repellant and preservative properties of the active agents for a long time without exposure to normal degrading agents. The pest-control formulation preferably comprises pesticide, repellant and preservative components, and a foaming and penetrating agent in a liquid carrier. The components are mixed with air to produce a foam that is injected directly into the inner spaces of walls, floors, ceilings or other above-ground structural members of the infested building. The foam is formulated with the objective of maximizing its absorption into the treated wood.

Because the active ingredients injected according to the invention remain contained in enclosed spaces above ground and removed from the soil, the method is effective regardless of the type of soil upon which a structure is built. Heat, soil alkalinity and water drainage, which normally degrade rather rapidly many otherwise effective control agents, do not materially affect the chemical agents injected according to the invention. Similarly, the invention minimizes the problem of water runoff carrying pest-control agents from the soil into underground aquifers. By placing the control agents into walls, rather than into the underlying soil, runoff contamination is virtually eliminated.

The method of the invention also provides a direct and more comprehensive pest-control strategy than prior-art approaches because the active agents carried in the foam injected above ground are spread throughout the infested areas and absorbed by the material exposed to the foam, including cracks and crevices that provide access to termites and other pests. This allows for complete coverage of all affected sites, providing initial destruction of pests present at the sites, and subsequent protection from future infestations by means of repellant and preservative ingredients absorbed into the structure.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiments and particularly pointed out in the claims. However, such drawings and description disclose only some of the various ways in which the invention may be practiced.

DETAILED DESCRIPTION OF THE PREFERRED EMBODIMENT

The present invention is the combination of several inventive concepts that together provide a significant improvement to the art of pest control. The invention is primarily directed to termite treatment and control. Therefore, the disclosure is presented in terms of termites, although it is understood that the same approach can be used in equivalent fashion to combat infestations by other insects.

The first aspect of the invention concerns the idea of treating directly the sites affected by termites in a structure with the objective of striking the termites locally at those sites, rather than treating the perimeter of the structure or the soil under the structure to create a boundary barrier and a poisonous environment affecting the termites generally at the boundary of the structure and at their colony. According to another aspect of the invention, after the initial extermination of the termite population treated at the infested sites, the objective is to render the termites' natural food supply undesirable and to repel them from returning to the sites, rather than to exterminate their colonies. In order to achieve this objective, the invention uses a pest-control formulation delivered as a foam that can be injected under pressure and forced to wet thoroughly and uniformly all areas in need of protection and impregnate deeply all treated material. The formulation consists of a novel combination of a termiticide with a wood preservative that produces a repellent effect on surviving termites. In essence, the heart of the invention is in the idea of removing the food source from the invading termites by impregnating it way beyond the surface of the material, rather than killing the termites' total population or creating a barrier to prevent the organism from returning to the food source, which are the approaches followed by all prior-art techniques.

The advantage of a foam over a liquid carrier is that it is much lighter and relatively seepage-free, although it behaves as a fluid and therefore can be used to spread uniformly through contiguous cavities to fill all empty space up to a desired elevation from the bottom plate, subflooring, concrete slab or other supporting structure separating the affected building from the underlying soil. In addition, since by definition a foam is a material in lightweight cellular form resulting from the introduction of air (or other gas) in a liquid, a relatively large surface area can be reached and wetted with a relatively small amount of liquid. By reducing the surface tension of the liquid, not only is the foaming process promoted but absorption of the foam into the wood fiber by capillary action is also greatly increased, thereby improving the process of impregnation. As the gas is liberated during the defoaming process, the liquid is left behind to wet and continue the process of impregnation of the material being treated.

Figure 1:
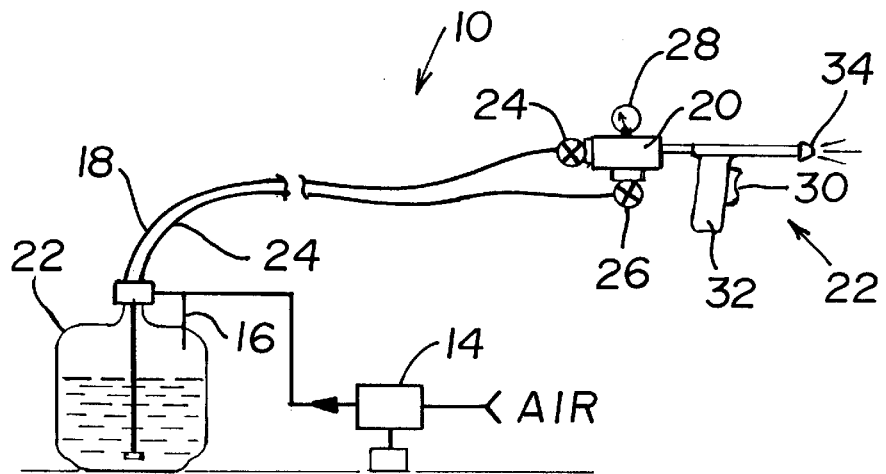
FIG. 1 is a schematic representation of injection equipment suitable for carrying out the foaming and pest-control treatment phases of the invention.

Referring to the drawings, wherein like parts are designated with like numerals and symbols, FIG. 1 is a schematic representation of injection apparatus 10 suitable for practicing the invention. The apparatus comprises a pressurized tank 12 for mixing the various components of the pest-control formulation used to treat a particular pest infestation. All chemicals are mixed in the tank 12 with a liquid carrier, such as water, and a surfactant to produce foaming of the mixture when contacted with a pressurized gas, such as air, and also designed to promote absorption of the foam and the liquid resulting therefrom into the wood being treated. A compressor 14 is used to pressurize the tank 12 through a line 16 such that the liquid mixture is forced to flow out of the tank through a flexible liquid delivery line 18 leading to a mixing chamber 20 incorporated into an application gun 22. A second line 24 with compressed air from the compressor 14 is run along the liquid line 18 to deliver air to the mixing chamber 20 and produce the foamed chemical mixture for injection according the invention. Appropriate valves 24,26 and a pressure gauge 28 are used to control the liquid/gas mixture in the mixing chamber 20 and produce the desired degree of foaming. For a given active-chemical composition and foaming agent, the optimal operating pressure and valve settings are determined empirically to deliver a predetermined volume of foam within a known time interval. Thus, the apparatus 10 can be calibrated to inject a known amount of chemicals in a known foam volume at a known rate simply by pressing a release trigger 30 in the handle 32 of the application gun 22.

Figure 2:
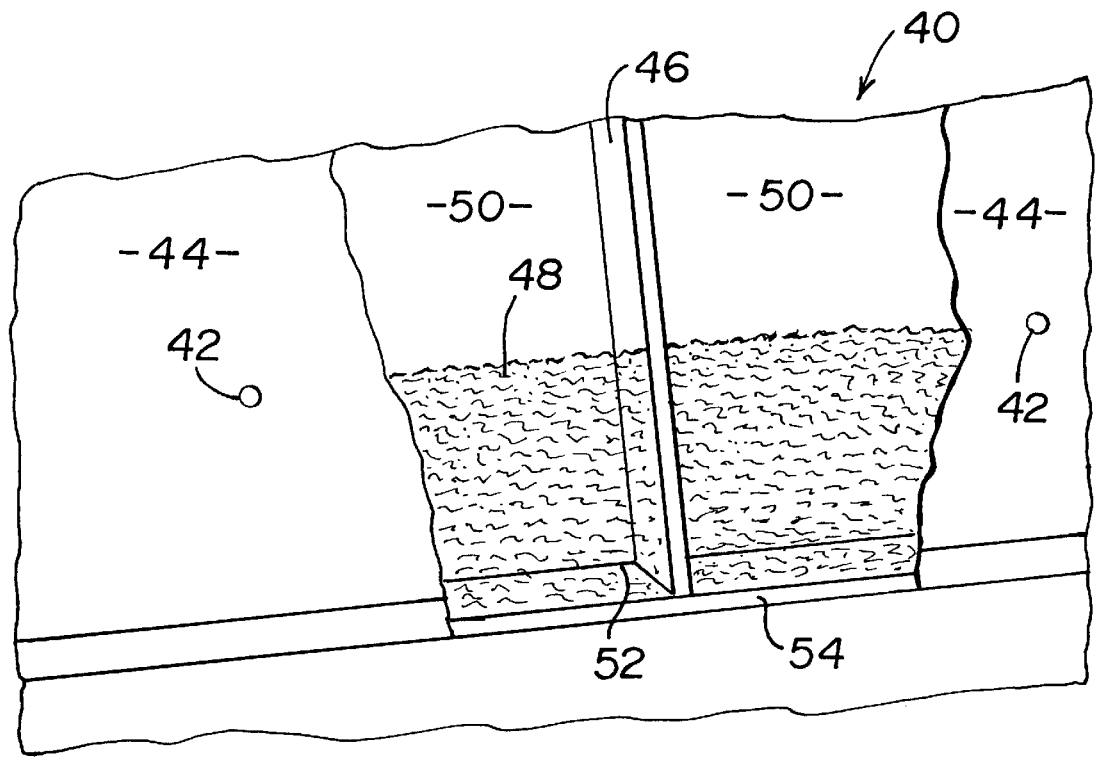
FIG. 2 is a partially cut-out view of a typical wallboard structure illustrating the application of a pest-control foam formulation according to the invention.

FIG. 2 illustrates the process of injection of the pest-control foam formulation in a partially cut-out wall according to the invention. A typical wall 40 of stud and wallboard construction is used for illustration. Injection holes 42, sufficiently large to accommodate the nozzle 34 of the applicator gun 22, are drilled into the wallboard panels 44 of the wall 40. At least one hole is drilled between each pair of studs 46 along the wall to cover at least the length affected by termites. As illustrated in the figure, a sufficient amount of foam 48 is injected to fill all the space between the front and back wallboard panels 44 and 50, respectively. Since the foam 48 is fluid, it fills all space available from the bottom of the wall, including cracks 52 in the bottom plate 54 (or in the subflooring or concrete slab) that may provide passage to termites from underground sources in the soil. The foam 48 reaches, wets and is absorbed by all interior surfaces within the structure of the wall 40, thereby impregnating them with termicidal, repellant and preservative agents that provide immediate extermination and subsequent protection from future recurrence of infestation. I found that a height of at least two to five inches of foam, preferably four inches, is required to provide the coverage necessary to prevent reinfestation of the structure.

The method of the invention is best implemented with a combination of a repellant agent, which may also have pesticidal properties, with a preservative component and a surfactant that enhances penetration of the mixture into porous materials. The combination of pyrethroids, such as permethrin and bifenthrin, and/or pyrethrins with borates and/or carbamates is particularly effective to treat subterranean termites. Pyrethroids and pyrethrins are known for their insecticidal and termite repellant properties. Borates and carbamates are also well known as wood preservatives that have some pesticidal activity, and they have before been used alternatively to permethrin and bifenthrin, but never in combination with them. I found that termites have not returned to consume wood impregnated with a combination of these substances as late as three years after treatment. Thus, the combination of the two classes of compounds in a foam that can reach and impregnate all infested areas of structural wood represents a novel approach in the treatment of infested wood and the prevention of recurring infestations. Chloronicotinyls (such as impidacloprid), sometimes preferred for their relatively low toxicity, may also be added to or used instead of pyrethroids and pyrethrins. I also found that the use of purified water, such as water purified by reverse osmosis, greatly enhances the effectiveness of the active ingredients by promoting foaming and penetration of the resultant mixture into the wood being treated.

In the preferred composition of the invention for the treatment of termites, about 8 fluid ounces of Termitafoam®, a surfactant sold by Univar of Kirkland, Wash., are mixed in tank 12 with about 64 fl oz of permethrin and about 32 oz av of disodium octaborate tetrahydrate in about 4 gallons of water. The order of mixing is crucial to obtaining the proper dissolution of the active ingredients in water, so that the mixture can penetrate the treated material. Accordingly, the surfactant must be well mixed with the water before the permethrin and borate are added. The mixture is then foamed in the mixing chamber 20 and injected into a wall through appropriate holes 42 drilled in the wallboard, as illustrated in FIG. 2. The volume of the area identified for treatment is estimated by calculation and the required foam formulation is injected for a time sufficient to fill that volume according to the calibrated throughput of the delivery equipment, as explained above. Adjacent areas likely to encounter similar infestation problems may be included for treatment with the infested areas. Obviously, after the structure has been treated with the foam formulation, all drilled injection points are preferably filled and refinished to repair any damage to the surface.

Using the preferred composition of the invention, an air pressure of about 30 psi in the mixing chamber 20 produces a foam having approximately 10 times the volume of the liquid composition. I found that in order to adequately impregnate the wood exposed to the foam, it must be sufficiently dense to remain around the treated surfaces for at least one hour. Thus, the properties and quantity of the foaming agent need be selected such as to produce a relatively-slow defoaming foam capable of maintaining its volume for at least one hour. If nonporous materials are present with the porous surfaces to be treated, such as pipes and other metallic structures, I found that the process is improved by foaming and injecting a portion of the treating solution at greater pressures, such as up to 45 psi, which produces a drier foam that adheres better to such nonporous material. Thus, after injecting about 80 to 90 percent of the desired foam at about 30 psi, the pressure in the mixing chamber 20 is raised to a higher value for foaming the remaining 10 to 20 percent.

The following examples illustrate the efficacy of the invention.

EXAMPLE 1

Johnston Atoll, located 800 miles southwest of Hawaii, is a National Wildlife Refuge that includes numerous buildings that stand on porous coral with an aquifer located about 7 ft under the ground surface. Initially, these buildings were found to be heavily infested with Formosan and Western termites, to the extent that even fiberglass insulation was penetrated. Construction materials for these structures varied from pine to asbestos and concrete block. Sub-slab injection and fumigation were prohibited in the refuge due to the unacceptable environmental risks associated with these practices.

To combat the termite infestation, an experimental composition was used in foam form with a chemical formulation consisting of about 0.5 wt. % permethrins and about 23 wt. % borates in a water solution. Three liquid ounces of a foaming solution containing alkyl ether sulfate ammonium salt in an alcohol carrier mixture of propanol and ethanol was then added to prepare each gallon of termiticidal composition. The composition was added to the tank of a FOAMGUARD® foamer, model FGW2SOO, manufactured by KO Manufacturing of Springfield, Mo. The air pressure was set at 30 psi, and the foam so produced was injected into the walls of the infested buildings through injection points spaced 0.5 to 1 foot apart, delivering approximately two gallons of foam into each. A 100% kill rate was achieved and no new infestations were found upon follow-up inspections with an insectascope even 30 months after treatment.

EXAMPLE 2

A slab home with termite infestation was treated by injecting a foam made by the following procedure. About 8 fluid ounces of the surfactant Termitafoam® were first mixed in about 4 gallons of R.O. water. After thoroughly mixing the surfactant in the water, about 64 fl oz of permethrin and about 32 oz av of disodium octaborate tetrahydrate were added and dissolved. The liquid mixture was then foamed at about 25–30 psi and injected into the treated walls above the slab through holes spaced about one foot apart. The foam was injected at a rate of about four gallons of foam every ten linear feet of wall. In areas containing pipes or electrical conduit, the last 10–20 percent of the foam was injected at a pressure of 35–45 psi.

This procedure was used during 1996 to treat in excess of 1,500 homes in Arizona, in an area where the normal rate of required retreat using conventional termite-control processes had been about 90 percent within 18 months of the initial treatment. The procedure of the invention required only about 10 percent retreat after the same period of time. Over 2,000 homes in the same area were treated in 1997, with less than five percent retreat being required during the first year after the initial application. These results represent a great improvement in the art.

Various changes in the details, steps and components that have been described may be made by those skilled in the art within the principles and scope of the invention herein illustrated and defined in the appended claims. For example, chemicals directed at exterminating and repelling other insects would be used instead of the ones disclosed here for termites. Similarly, preservatives for materials other than wood would be utilized as required for a particular application.

Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

I claim:

1. A method of applying a termiticide to protect a wall section of a structure affected by termite infestation, wherein said structure is built on a concrete slab or footing and said wall section includes spaced-apart wooden members and a wallboard panel defining above-ground cavities between the wooden members in the wall section, the method comprising the following steps:

mixing the termiticide with a foamable carrier to produce a flowable termiticidal foam adapted for impregnation of the wooden members;

providing a plurality of holes in the wallboard panel;

injecting the termiticidal foam into the above-ground cavities of said wall section of the structure affected by termite infestation in order to flood the cavities and form a continuous foam layer in the wall section above said slab or footing and impregnate the wooden members contacted by the termiticidal foam; and filling said plurality of holes in the wallboard panel.

2. The method of claim 1, wherein said pest-control agent comprises a pesticide and a wood preservative.

3. The method of claim 1, wherein said foamable carrier comprises a surfactant mixed in water.

4. The method of claim 3, wherein said water is purified by reverse osmosis.

5. The method of claim 1, wherein said pest-control agent comprises a pesticide and a wood preservative and said foamable carrier comprises a surfactant mixed in water.

6. The method of claim 5, wherein said water is purified by reverse osmosis.

7. The method of claim 1, wherein said termiticide is selected from the group consisting of pyrethroids, pyrethrins, and mixtures thereof, and the termiticide is combined with a wood preservative selected from the group consisting of borates, carbamates, and mixtures thereof.

8. The method of claim 7, wherein said foamable carrier comprises a surfactant mixed in water.

9. The method of claim 8, wherein said water is purified by reverse osmosis.

10. The method of claim 7, wherein said termiticide comprises about 0.5 wt. % permethrin and said wood preservative comprises about 23 wt. % borates.

11. The method of claim 9, wherein said termiticide comprises about 0.5 wt. % permethrin and said wood preservative comprises about 23 wt. % borates.

12. The method of claim 7, wherein said mixing step is carried out at a pressure of about 25 to 45 psi.

13. The method of claim 11, wherein said mixing step is carried out at a pressure of about 25 to 45 psi.

\* \* \* \* \*